US00PP21106P2

(12) United States Plant Patent
Hoek

(10) Patent No.: US PP21,106 P2
(45) Date of Patent: Jun. 29, 2010

(54) ***CHRYSANTHEMUM* PLANT NAMED 'ANASTASIA DARK GREEN'**

(50) Latin Name: *Chrysanthemum×morifolium*
Varietal Denomination: Anastasia Dark Green

(75) Inventor: Jan Hoek, 's-Gravenzande (NL)

(73) Assignee: Deliflor Chrysanten B.V., Maasdijk (NL)

( * ) Notice: Subject to any disclaimer, the term of this patent is extended or adjusted under 35 U.S.C. 154(b) by 0 days.

(21) Appl. No.: 12/383,847

(22) Filed: Mar. 27, 2009

(51) Int. Cl.
*A01H 5/00* (2006.01)

(52) U.S. Cl. ..... Plt./284

(58) Field of Classification Search ..... Plt./284
See application file for complete search history.

*Primary Examiner*—Annette H Para
(74) *Attorney, Agent, or Firm*—C. A. Whealy

(57) ABSTRACT

A new and distinct cultivar of *Chrysanthemum* plant named 'Anastasia Dark Green', characterized by its large double-type inflorescences with incurved quilled green-colored ray florets; strong and erect flowering stems; low number of lateral branches; dark green-colored leaves; quick flowering response; and good postproduction longevity.

2 Drawing Sheets

Botanical designation: *Chrysanthemum×morifolium.*
Cultivar denomination: 'ANASTASIA DARK GREEN'.

BACKGROUND OF THE INVENTION

The present invention relates to a new and distinct cultivar of *Chrysanthemum* plant, botanically known as *Chrysanthemum×morifolium*, commercially grown as a cut flower and hereinafter referred to by the name 'Anastasia Dark Green'.

The new *Chrysanthemum* plant is a naturally-occurring whole plant mutation of *Chrysanthemum ×morifolium* 'Anastasia Green', disclosed in U.S. Plant Pat. No. 18,032. The new *Chrysanthemum* was discovered and selected by the Inventor as a single flowering plant from within a population of plants of 'Anastasia Green' in a controlled greenhouse environment in Maasdijk, The Netherlands in March, 2007.

Asexual reproduction of the new *Chrysanthemum* by terminal cuttings in a controlled greenhouse environment in Maasdijk, The Netherlands since March, 2007, has shown that the unique features of this new *Chrysanthemum* are stable and reproduced true to type in successive generations.

SUMMARY OF THE INVENTION

Plants of the new *Chrysanthemum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Anastasia Dark Green'. These characteristics in combination distinguish 'Anastasia Dark Green' as a new and distinct cultivar of *Chrysanthemum:*

1. Large double-type inflorescences with incurved quilled green-colored ray florets.
2. Strong and upright flowering stems.
3. Low number of lateral branches.
4. Dark green-colored leaves.

5. Quick flowering response; plants flower about 53 to 56 days after the start of photoinductive treatments.
6. Good postproduction longevity; plants maintain good substance for about four weeks in an interior environment.

Plants of the new *Chrysanthemum* differ from plants of the parent, 'Anastasia Green', primarily in ray floret color as plants of 'Anastasia Green' have lighter green-colored ray florets. In addition, ray florets of plants of the new *Chrysanthemum* are curved over the length of the floret whereas ray florets of plants of 'Anastasia Green' are only curved at the apices.

Plants of the new *Chrysanthemum* can be compared to plants of *Chrysanthemum×morifolium* 'Shamrock', disclosed in U.S. Plant Pat. No. 4,884. In side-by-side comparisons conducted in Maasdijk, The Netherlands, plants of the new *Chrysanthemum* differed from plants of 'Shamrock' in the following characteristics:

1. Plants of the new *Chrysanthemum* had fewer lateral branches than plants of 'Shamrock'.
2. Plants of the new *Chrysanthemum* had fewer leaves than plants of 'Shamrock'.
3. Plants of the new *Chrysanthemum* had darker green-colored leaves than plants of 'Shamrock'.
4. Plants of the new *Chrysanthemum* flowered two weeks earlier than plants of 'Shamrock'.

BRIEF DESCRIPTION OF THE PHOTOGRAPHS

The accompanying colored photographs illustrate the overall appearance of the new *Chrysanthemum* plant. These photographs show the colors as true as it is reasonably possible to obtain in colored reproductions of this type. Colors in the photographs may differ slightly from the color values cited in the detailed botanical description which accurately describe the colors of the new *Chrysanthemum* plant.

The photograph on the first sheet comprises a side perspective view of a typical flowering stem of 'Anastasia Dark Green' grown as a disbud type.

The photograph on the second sheet comprises close-up views of the upper surface (top left of photograph) and lower surface (bottom left of photograph) of typical inflorescences of 'Anastasia Dark Green' and the upper and lower surfaces of fully expanded leaves (top right of photograph) and upper and lower surfaces of developing leaves (bottom right of photograph) of 'Anastasia Dark Green'.

DETAILED BOTANICAL DESCRIPTION

The aforementioned photographs and following observations and measurements describe plants grown during the winter in Maasdijk, The Netherlands, under commercial practice in a glass-covered greenhouse. Plants were initially given 16 days of long day/short night treatments followed by short day/long night treatments to induce flower initiation and development. During the production of the plants, day temperatures ranged from 18° C. to 25° C., night temperatures ranged from 20° C. to 22° C. and light levels were about 7 kilolux. Plants had been growing for eleven weeks when the photographs and the description were taken. In the following description, color references are made to The Royal Horticultural Society Colour Chart, 2001 Edition, except where general terms of ordinary dictionary significance are used.

Botanical classification: *Chrysanthemum×morifolium* 'Anastasia Dark Green'.

Parentage: Naturally-occurring whole plant mutation of *Chrysanthemum×morifolium* 'Anastasia Green', disclosed in U.S. Plant Pat. No. 18,032.

Propagation:

*Type.*—Terminal vegetative cuttings.

*Time to initiate roots, summer.*—About six days at 20° C.

*Time to initiate roots, winter.*—About seven days at 20° C.

*Time to produce a rooted young plant, summer.*—About 13 days at 20° C.

*Time to produce a rooted young plant, winter.*—About 15 days at 20° C.

*Root description.*—Fine, fibrous; light brown in color.

*Rooting habit.*—Freely branching, moderately dense.

Plant description:

*Appearance/growth habit.*—Herbaceous double-type cut flower that is typically grown as a disbud-type; moderately vigorous growth habit.

*Flowering stem description.*—Aspect: Erect. Length: About 80 cm to 90 cm. Diameter: About 5 mm to 7 mm. Quantity of lateral branches: About 10 to 15. Lateral branch length: About 10 cm to 20 cm. Lateral branch diameter: About 4 mm to 7 mm. Internode length: About 2.5 cm to 3.5 cm. Strength: Strong. Texture: Pubescent; longitudinally ridged. Color: Close to 146B.

*Foliage description.*—Arrangement: Alternate; simple. Length: About 10 cm to 16 cm. Width: About 6 cm to 12 cm. Apex: Acute. Base: Attenuate. Margin: Palmately lobed; sinuses divergent. Texture, upper and lower surfaces: Pubescent, rough; veins prominent on lower surface. Venation pattern: Pinnate, reticulate. Color: Developing leaves, upper surface: Close to 137B. Developing leaves, lower surface: Close to 146B. Fully developed leaves, upper surface: Between 147A and 137A; venation, close to 147B. Fully developed leaves, lower surface: Close to 147B; venation, close to 146B. Petiole: Length: About 2 cm to 3 cm. Diameter: About 3 mm. Texture, upper surface: Rough. Texture, lower surface: Slightly rough. Color, upper surface: Between 147B and 146B. Color, lower surface: Close to 146B to 146C.

Inflorescence description:

*Appearance.*—Large double-type inflorescence form with incurved quilled-shaped ray florets; typically grown as a disbud with one inflorescence allowed to develop per terminal; ray and disc florets develop acropetally on a capitulum.

*Fragrance.*—Moderate to strong.

*Flowering response.*—Under natural conditions, plant flower in the autumn/winter in the Northern Hemisphere; at other times of the year, inflorescence initiation and development can be induced under short day/long night conditions (at least 13.5 hours of darkness); quick flowering response; plants flower about 53 to 56 days after the start of photoinductive treatments when grown as a disbud-type.

*Postproduction longevity.*—In an interior environment, inflorescences and foliage will maintain good color and substance for about four weeks; inflorescences persistent.

*Inflorescence size.*—Diameter: About 10 cm. Depth (height): About 4 cm. Disc diameter: Not visible. Receptacle height: About 4 mm. Receptacle diameter: About 1 cm to 1.2 cm. Receptacle color: Close to 144C.

*Inflorescence buds.*—Shape: Flattened spherical. Height: About 7 mm. Diameter: About 1.3 cm. Color: Close to 137C.

*Ray florets.*—Length: About 3.5 cm to 5 cm. Width: About 2 mm to 4 mm. Shape: Quilled, incurved. Apex: Emarginate. Base: Fused, tubular. Texture, upper and lower surfaces: Smooth, glabrous; satiny. Number per inflorescence: About 275 arranged in numerous whorls. Color: When opening, upper and lower surfaces: Close to 145B. Fully opened, upper and lower surfaces: Close to 144B; color becoming closer to 145B with development.

*Disc florets.*—Shape: Fused tubular, elongated. Apex: Rounded. Length: About 7 mm. Diameter: About 1 mm. Number per inflorescence: None or occasionally one. Color: Apex: Close to 144A. Mid-section: Close to 14C. Base: Close to 145D.

*Involucral bracts.*—Length: About 9 mm to 13 mm. Width: About 2 mm to 6 mm. Shape: Ovate. Apex: Obtuse. Base: Truncate. Margin: Entire. Texture, upper surface: Smooth, glabrous. Texture, lower surface: Pubescent; slightly rough. Number per inflorescence: About 50 arranged in about four whorls. Color, upper surface: Close to 137B to 137C. Color, lower surface: Close to 137A to 137B.

*Peduncles.*—Length: About 4 cm. Diameter: About 4 mm to 5 mm. Angle: Erect. Strength: Strong. Texture: Pubescent; longitudinally ridged. Color: More green than 147B.

*Reproductive organs.*—Androecium: Not observed. Gynoecium: Not observed.

*Seed/fruit.*—Seed and fruit production has not been observed.

Disease/pest resistance: Resistance to pathogens and pests common to *Chrysanthemums* has not been observed on plants grown under commercial conditions.

It is claimed:

1. A new and distinct *Chrysanthemum* plant named 'Anastasia Dark Green' as illustrated and described.

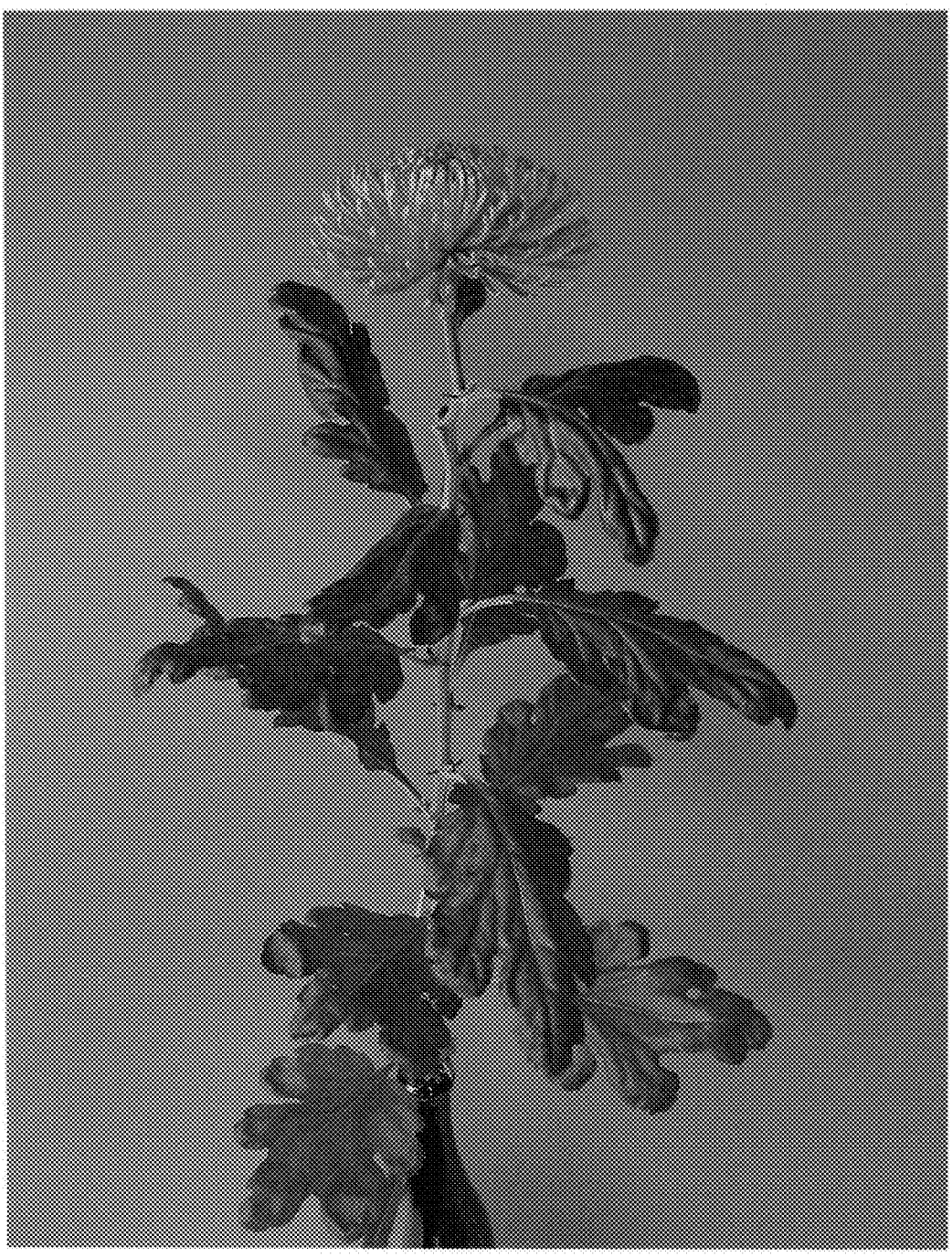

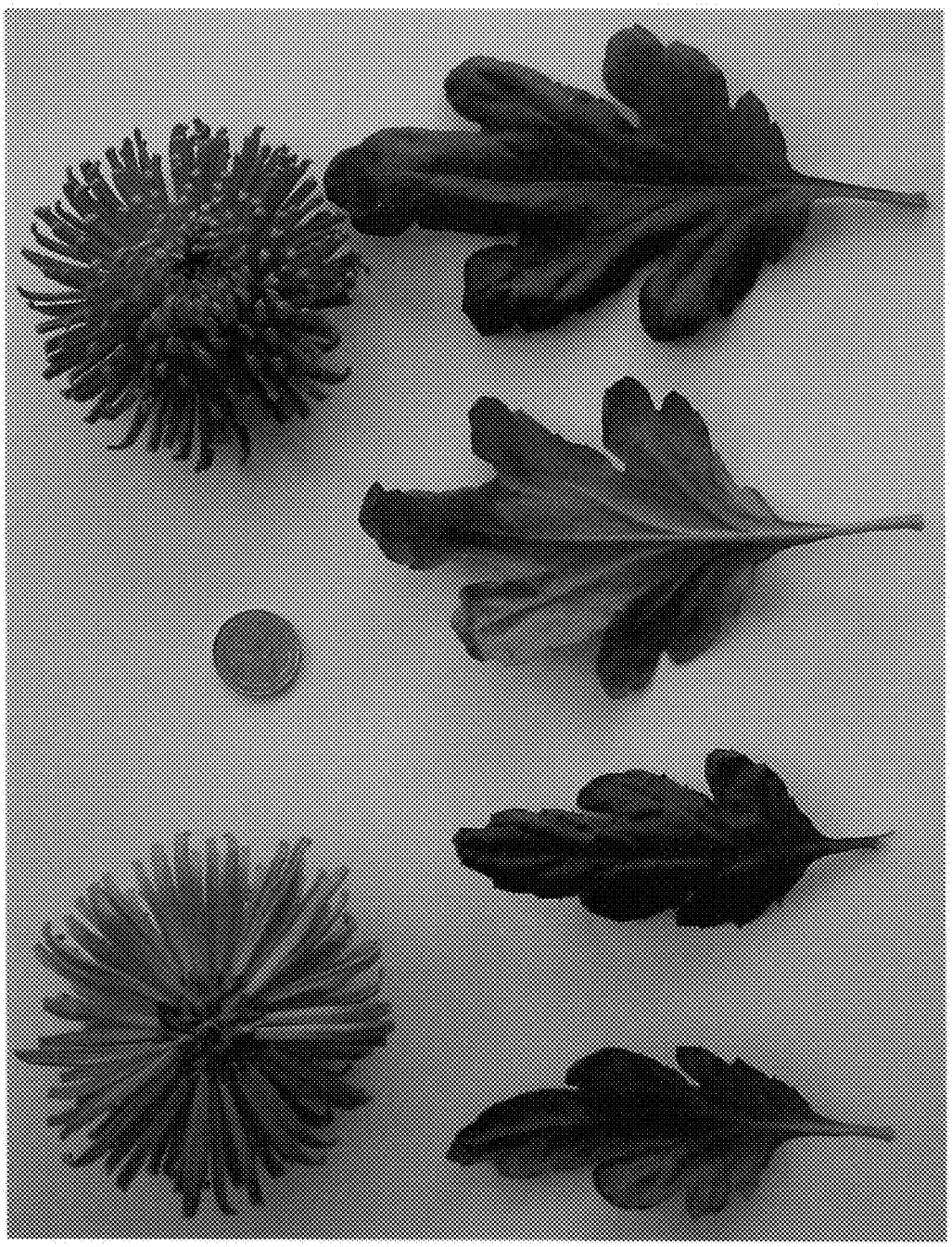

* * * * *